(12) United States Patent
Cheek et al.

(10) Patent No.: US 9,429,563 B2
(45) Date of Patent: Aug. 30, 2016

(54) MULTI-ZONE FALLING WASHER BLOOD CLOT DETECTION

(71) Applicant: Medtronic, Inc., Minneapolis, MN (US)

(72) Inventors: Daniel Cheek, Plymouth, MN (US); Lawrence Erickson, Brooklyn Park, MN (US); Trevor Huang, Maple Grove, MN (US); Tessy Kanayinkal, Brooklyn Park, MN (US); Craig Petersen, Brooklyn Park, MN (US); Charlene Yuan, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/706,453

(22) Filed: Dec. 6, 2012

(65) Prior Publication Data

US 2013/0144538 A1 Jun. 6, 2013

Related U.S. Application Data

(60) Provisional application No. 61/567,389, filed on Dec. 6, 2011.

(51) Int. Cl.
*G01N 33/49* (2006.01)
(52) U.S. Cl.
CPC .................................. *G01N 33/4905* (2013.01)

(58) Field of Classification Search
None
See application file for complete search history.

(56) References Cited

U.S. PATENT DOCUMENTS

| 4,289,498 A * | 9/1981 | Baughman et al. ............ 436/34 |
| 5,441,892 A * | 8/1995 | Baugh ............................. 436/69 |
| 5,629,209 A | 5/1997 | Braun, Sr. et al. |
| 6,613,286 B2 | 9/2003 | Braun, Sr. et al. |
| 2011/0039285 A1* | 2/2011 | Sadaba Champetier De Ribes et al. ............................. 435/13 |

FOREIGN PATENT DOCUMENTS

WO WO2006/100443 9/2006

* cited by examiner

*Primary Examiner* — Eric S Dejong
*Assistant Examiner* — G. Steven Vanni

(57) ABSTRACT

Activated clotting time (ACT) tests detect blood clotting time based on the viscosity changes of a test sample, using a ferromagnetic washer lifted to the top of a test chamber and then dropped from the top via gravity; a drop time greater than a preset threshold value indicates clotting of the test sample. Blood samples which have high levels of heparin usually produce very weak clots that may easily be destroyed by the lifting movement of the washer. But if the clot threshold is set low to detect the weak clots, false detections occur during early testing cycles when activators are not fully suspended during the mixing cycle. Improved algorithms for lifting the washer and adjusting over time enable accurate detection of weak clots.

6 Claims, 17 Drawing Sheets

MULTI-ZONE FALLING WASHER BLOOD CLOT DETECTION

RELATED APPLICATIONS

This application claims the benefit of U.S. Provisional Patent Application 61/567,389 filed Dec. 6, 2011, the disclosure of which is herein incorporated by reference in its entirety.

TECHNICAL FIELD

This invention relates to detecting changes in viscosity of biologic fluid test samples, e.g., detecting coagulation and coagulation-related activities including agglutination and fibrinolysis of human blood test samples, and more particularly to improved methods and apparatus for obtaining a coagulation time of a blood test sample.

BACKGROUND

Blood coagulation is a complex chemical and physical reaction that occurs when blood comes into contact with an activating agent, such as an activating surface or an activating agent. (In this context, the term "blood" means whole blood, citrated blood, platelet concentrate, plasma, or control mixtures of plasma and blood cells, unless otherwise specifically called out otherwise; the term particularly includes heparinized blood.)

Several tests of coagulation are routinely utilized to assess the complicated cascade of events leading to blood clot formation and test for the presence of abnormalities or inhibitors of this process. Among these tests are activated clotting time (ACT), which includes high range ACT (HRACT), a test which features a slope response to moderate to high heparin levels (up to 6 U/mL) in whole blood drawn from a patient during cardiac surgery. The ACT test formulated to respond to low heparin levels (0.1 to 1.0 U/mL) in whole blood drawn from a patient during the extracorporeal membrane oxygenation (ECMO) procedure is low range ACT (LRACT), which is also in the scope of this application.

Unfractionated heparin is most commonly used for anticoagulation during cardiac pulmonary bypass (CPB) surgery to prevent gross clotting of the bypass circuit and more activation and consumption of coagulation system components. While an ACT test responds to heparin, it is a global assessment of coagulation status of blood and affected by many other factors other than heparin, such as hemodilution and temperature. Due to the limitation of ACT monitoring and the variability of patient response to heparin dose, individualized heparin and protamine management based on heparin protamine titration test has associated with improved clinical outcomes. The heparin protamine titration test uses activated clotting time as test end point, which is also in the scope of this application.

During heart bypass surgery, the platelets of blood circulated in an extracorporeal circuit may become activated by contact with the materials present in the extracorporeal circuit. This activation may be reversible or irreversible. Once platelets are irreversibly activated, they lose their ability to function further. A deficiency of functional platelets in the blood may be indicative of an increased probability of a post-operative bleeding problem. Such a deficiency, and the resulting post-operative bleeding risk, could be remedied by a transfusion of platelet concentrate. Platelet functionality tests, which can use activated clotting time as a test end point, can identify a deficiency of platelets or functional platelets and aid the attending surgeon in ascertaining when to administer a platelet concentrate transfusion. Such a test is further useful in ascertaining the efficacy of a platelet transfusion. By performing the platelet functionality test following a platelet transfusion, it is possible to determine if additional platelet concentrate transfusions are indicated. Real-time assessment of clotting function at the operative site may be performed to evaluate the result of therapeutic interventions and also to test and optimize, a priori, the treatment choice and dosage.

Other anticoagulant drugs used in cardiac surgery and cardiac catheterization procedures, such as low molecular weight heparin and bivalirudin, are also monitored with activated clotting time. The clotting time test used to monitor bivalirudin uses ecarin as activator, thus the test is called ecarin time (ECT). This application works with all clot time based tests.

ACT tests described in this application are based on the viscosity change of a test sample within a test chamber. During a test cycle, a ferromagnetic washer immersed in the test sample is lifted to the top of the test chamber by magnetic force produced by a magnetic field located at the top of the test chamber; the washer is then held at the top of the test chamber for a specific time. After the specified holding time, the washer is then dropped through the test sample via gravity. The increased viscosity due to the clotting of the test sample slows the motion of the washer. Thus, if the time that the washer travels through a specified distance (i.e., the washer "drop time") is greater than a preset value (the clot detection sensitivity threshold), a clot is detected and an ACT value is reported.

A particular apparatus and method for detecting changes in human blood viscosity based on this principle is disclosed in U.S. Pat. Nos. 5,629,209 and 6,613,286, in which heparinized blood is introduced into a test cartridge through an injection port and fills a blood receiving/dispensing reservoir. The blood then moves from the reservoir through at least one conduit into at least one blood-receiving chamber where it is subjected to a viscosity test. A freely movable ferromagnetic washer is also located within the blood-receiving chamber that is moved up using an electromagnet of the test apparatus and allowed to drop with the force of gravity. Changes in the viscosity of the blood that the ferromagnetic washer falls through are detected by determining the position of the ferromagnetic washer in the blood-receiving chamber in a given time, or by a given number of rises and falls of the ferromagnetic washer. Air in the conduit and blood-receiving chamber is vented to atmosphere through a further vent conduit and an air vent/fluid plug as the blood sample is fills the blood-receiving chamber.

The movement of the washer in the above approach is actively controlled only when it is moved up, and the washer passively drops with the force of gravity. The washer is free to float in the test chamber and may drift side-to-side as it is moved up or floats downward. The side-to-side drifting movement may affect the rise time and the fall time, which could add error to the coagulation time measured. The washer may eventually stop moving as a clot forms about it, and no additional information can be obtained on the coagulation process in the sample.

SUMMARY

It has been discovered that, in a blood sample that is heparinized with high level of heparin, the clots produced by the contact pathway activation (the kind of activation typically used for HR-ACT) are usually very weak; the clot is easily destroyed by the lifting movement of the washer. The weak clot also produces less change in test fluid viscosity, which requires the clot threshold to be set at a very low value to detect the weak clots. The low clot detection sensitivity threshold produces false detection during the early testing cycles when the dried kaolin activators are not fully suspended during the mixing cycle. This may cause a slower washer drop time as compared to later test cycles when the activators are more thoroughly suspended.

It has been further discovered that protection against, and detection of, weakly formed clots may be achieved by using a clot protection and detection algorithm to control the measurement apparatus. In general terms, one such algorithm calculates a clot detection threshold based on measurement of the washer drop times in a small number of initial cycles; in addition, the entire washer drop distance is divided into a plurality of zones and drop times are measured in each, then summed into a value which is multiplied by a scale factor for each zone. The scale factor may or may not be constant throughout the entire test; in one embodiment, the scale factor (and thus the clot threshold for that zone) is reduced during later test cycles. Specifically, the test duration is divided into three test periods. During the initial period, the clot detection sensitivity threshold is a relatively higher constant value based on the viscosity (washer drop time) of the test cycles after sample mixing; the higher clot detection sensitivity threshold during this first period (on the order of 30 to 100 seconds for HR-ACT) avoids early clot detection. The clot detection sensitivity threshold is then reduced during a transition period (between about 30 to 100 sec and about 400 to 500 seconds). Finally, in the last period, the clot detection sensitivity threshold stays at the relatively lower (but again constant) value to ensure detection of weak clots. Adjustment of the clot detection threshold detects weak clots that may otherwise be destroyed or falsely detected. Thus, in general terms, one may detect formation of a clot in a sample with a washer moving the sample when the blood is not clotted, by comparing a time with which the washer moves through each of the zones to a product of a scale factor and a sum of times taken by the washer to move through each of the zones on a plurality of prior occasions. The scale factor may or may not be constant over time.

Another algorithm does not employ zones, and further (in contrast to the first algorithm), relies on a calculation of disk velocity as the dependent variable, taking distance as the independent variable and a fixed time value as a constant. Calibration values are determined for each of a distance span and a drop velocity of the washer moving through the sample when the blood is not clotted. Repeated measurements of the distance span and the drop velocity of the washer moving through the sample in a single cycle are made, and the clot is detected when any of a plurality of criteria based upon the values of distance span and drop velocity are met. For further confidence that a clot has been detected, it is possible to require the detection threshold to be reached for a plurality of consecutive cycles before a clot is declared. It is also possible to vary a parameter relevant to at least one of the plurality of criteria over a series of the repeated measurements.

This summary of the claims has been presented here simply to point out some of the ways that the claims overcomes difficulties presented in the prior art and to distinguish the claims from the prior art and is not intended to operate in any manner as a limitation on the interpretation of claims that are presented initially in the patent application and that are ultimately granted.

BRIEF DESCRIPTION OF THE DRAWINGS

These and other advantages and features will be more readily understood from the following detailed description of various embodiments, when considered in conjunction with the drawings, in which like reference numerals indicate identical structures throughout the several views, and in which.

DETAILED DESCRIPTION

In the following detailed description, references are made to illustrative embodiments of methods and apparatus for carrying out the claims. It is understood that other embodiments can be utilized without departing from the scope of the claims. Illustrative methods and apparatus are described for performing blood coagulation tests of the type described above.

Figure 1:
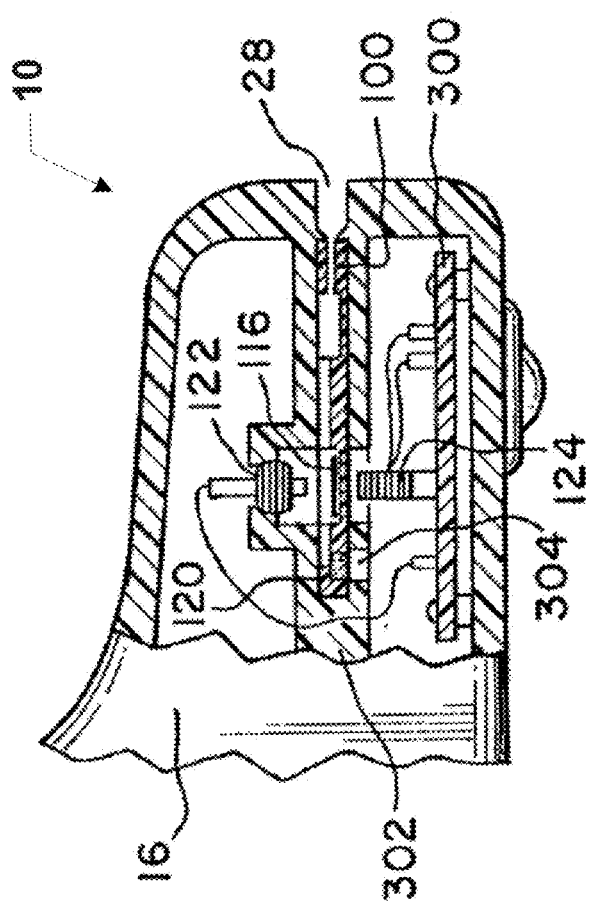
FIG. 1, which is based on FIG. 13 of U.S. Pat. No. 5,629,209, is a cross-sectional view of a cartridge positioned within a machine.

FIG. 1 only illustrates the basic features of a possible apparatus or system, as known from U.S. Pat. No. 5,629,209, the entirety of which is incorporated by reference. The cartridge 100, having been inserted into the side 16 of the machine 10, is secured within the cartridge holder 302. An aperture 28 enables the fluid sample to be introduced into the cartridge 100 after the cartridge 100 is inserted into the machine 10. An air vent/fluid plug device 120 is aligned over a hole 304 in the base of the cartridge holder 302 to permit escape of air that is vented from the cartridge 100 during the movement of the fluid sample into its respective fluid-receiving chamber. Each fluid-receiving chamber is typically associated with a means for moving the ferromagnetic material (e.g., a washer made of a ferromagnetic material) provided by the machine 10, such as an electromagnet 122, and a means for detecting the position of the ferromagnetic material 116 within the chamber 114, e.g., a detector 124. A radio frequency detector may be conveniently employed for this purpose. It should be noted that the detector 124 is not limited to the detection of ferromagnetic material but is capable of detecting any metallic substance placed within the chamber 114. The electromagnet 122 and the position detector 124 are connected to a circuit board 300 and thereby operatively connected to an associated computer processor (not shown) which receives information, provides directions, and calculates intermediate or final values relevant to the tests. The processor is under control of programming executed by the processor as required. For simplicity of illustration, only one fluid-receiving chamber 114, electromagnet 122, and position detector 124 are shown. Cartridge 100 may have a plurality of such arrangements for alternative and/or comparative tests.

Figure 2:
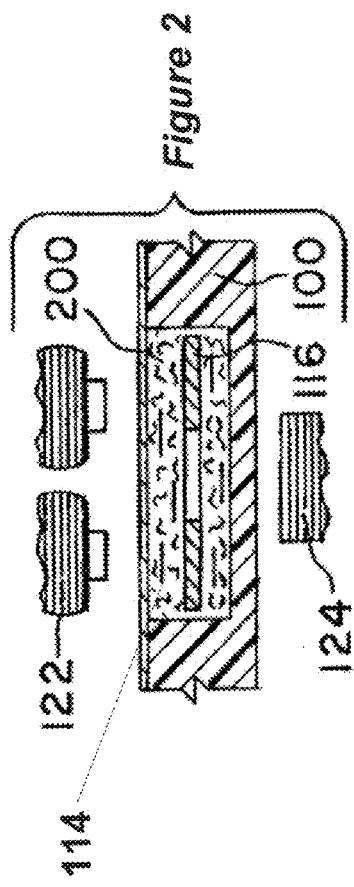
FIG. 2, which is based on FIG. 12d of U.S. Pat. No. 5,629,209, is a partial cross-sectional view of the cartridge of FIG. 1.

FIG. 2 illustrates that fluid 200 fills the fluid-receiving chamber and reaches the air vent/fluid plug device 120 to establish a fluid lock. Ferromagnetic washer 116 is moved between a resting position on the bottom of the fluid-receiving chamber 114 and the top of the chamber 114 as the electromagnet 122 is energized; if the electromagnet 122 is turned off the washer 116, under the force of gravity, falls through the fluid 200 to the bottom of the chamber 114. The position detector 124 measures the time required for the washer 116 to fall from the top to the bottom of the chamber 114 and sends this information to the associated computer. As the viscosity of the fluid 200 increases, the measured time increases. Indeed, in the case of blood coagulation, eventually, a washer 116 is unable to move through a blood sample.

When the fluid 200 whose viscosity is being measured is blood, the motion of the washer 116 through the blood also has the effect of activating the clotting process of the blood. The activation effect is enhanced when the surface of the washer 116 is roughened in known ways, as such techniques increase the surface area of the washer. If even faster clotting times are necessary, a viscosity-altering substance may be used. For example, a clotting activator such as tissue factor thromboplastin can be added to the cartridge, or a particulate activator such as diatomaceous earth or kaolin may be used either alone or in combination with other activators such as phospholipids or tissue factors.

The position detector 124 in one embodiment is a radio frequency detector. Radio frequency detectors sense the position of the washer 116 by sensing the changes in the magnetic field surrounding the detection coil of the radio frequency detector that are caused by the presence of the washer 116. Radio frequency detectors have sensitivity to ferromagnetic and other metallic materials and resistance to effects caused by other elements of the device, such as the fluid. It should be understood, however, that other types of position detectors 124 are contemplated. For example, in another embodiment, the position detector 124 is a Hall effect sensor and its associated circuitry, as generally described in U.S. Pat. No. 7,775,976 (the entirety of which is incorporated by reference) at column 16, line 15 to column 17, line 5. Regardless of the type of position detector 124 employed, the absolute position of the washer 116 is measured and used as described below.

The invention may be practiced in various embodiments, which are discussed individually below solely for convenience. Features from one embodiment may be combined with features from another embodiment (applying, if necessary or desirable, whatever modifications would be understood by one of ordinary skill after reading this description), without departing from the full scope of the invention.

In a typical sequence, a test cartridge 100 is inserted into the side 16 of the machine 10 through the slot 26, and the washer 116 is lifted and dropped a number (such as three) times by electromagnet 122. This provides the average values for the minimum and maximum distances that washer 116 travels without test fluid 200. This process also serves as a system self test to verify the functions of cartridge 100 and machine 10.

After the initial testing, a sample mix cycle begins the test protocol. The electromagnet 122 initially raises and lowers the washer 116 rapidly several times to further mix the fluid 200 with any viscosity-altering substance present and, if the fluid 200 is blood, promote activation of clotting, as discussed above. The fluid 200 is then allowed to rest for a short time, the duration of which depends on test type. For example, in a heparin protamine titration test, the test cycle may be initiated immediately after the sample mix cycles.

During the subsequent test itself, the electromagnet 122 raises the washer 116 repeatedly at a slower rate and/or reduced lifting power. After each elevation of the washer, the position detector 124 is used to determine the "fall time" (or "drop time"), i.e., the time taken for the washer 116 to fall to the bottom of the chamber 114. Absence of an increase in fall time suggests a lack of coagulation and the test continues. But an increase in fall time suggests a change in viscosity, measured in terms of the amount of fall time as compared to a baseline value. All data, including individual test results, may be displayed, stored in memory, printed, or sent to another computer, or any combination of the same.

Figure 3:
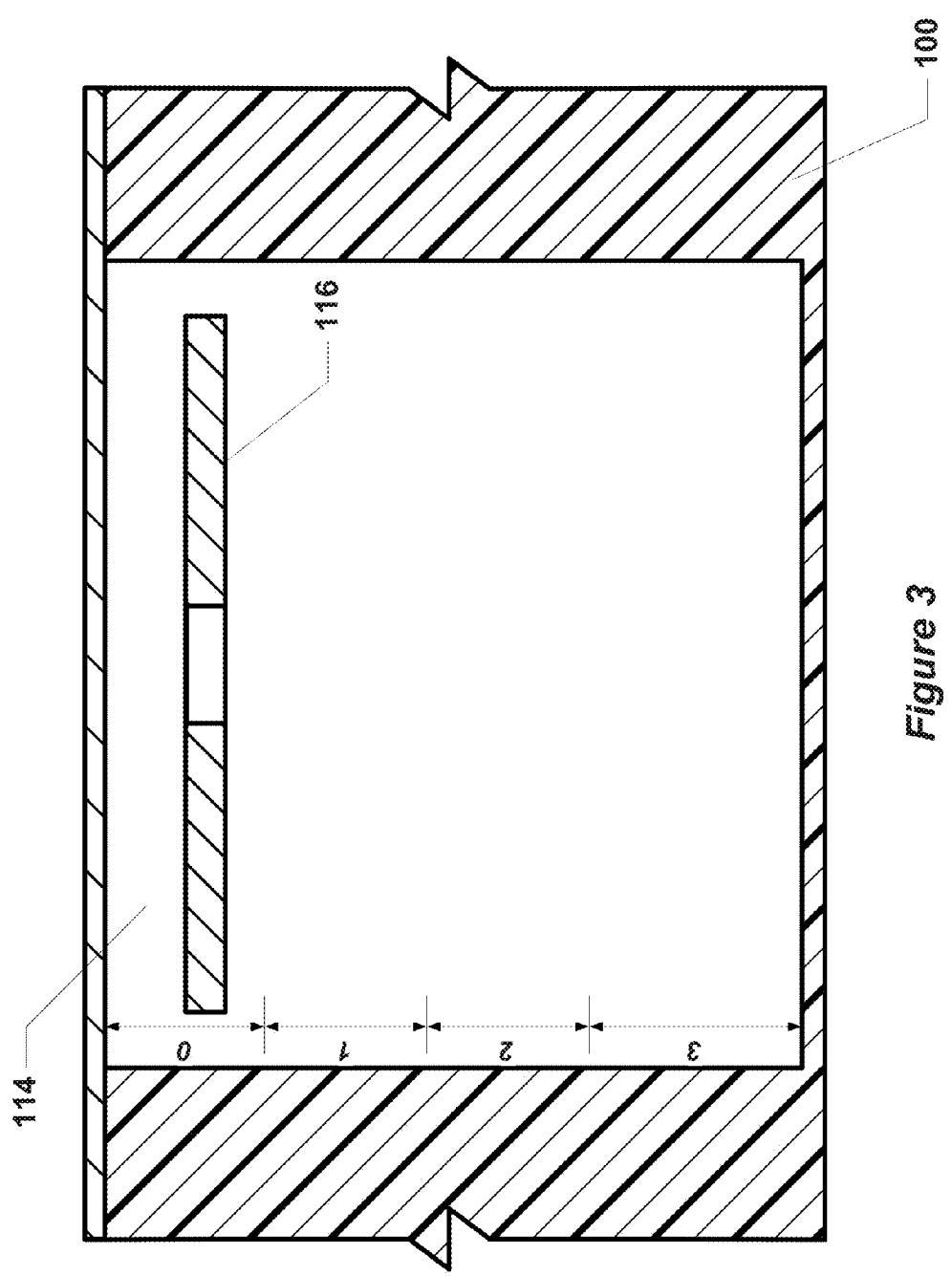
FIG. 3 is a schematic cross-section of the test chamber portion of the cartridge of FIGS. 1 and 2.
Figure 4A:
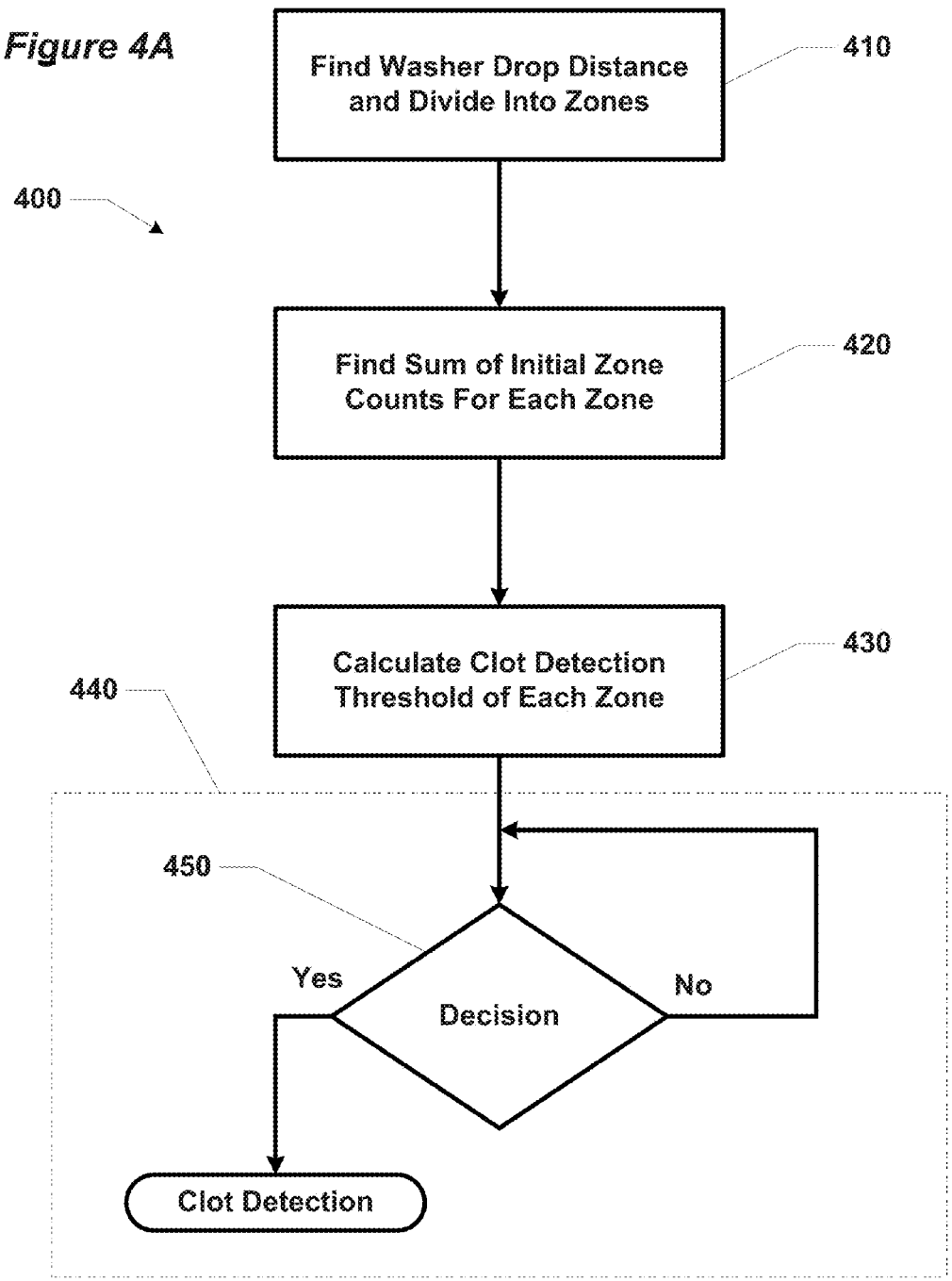
FIG. 4A is a flowchart of a first embodiment, a portion of which is shown in greater detail in FIG. 4B
Figure 4B:
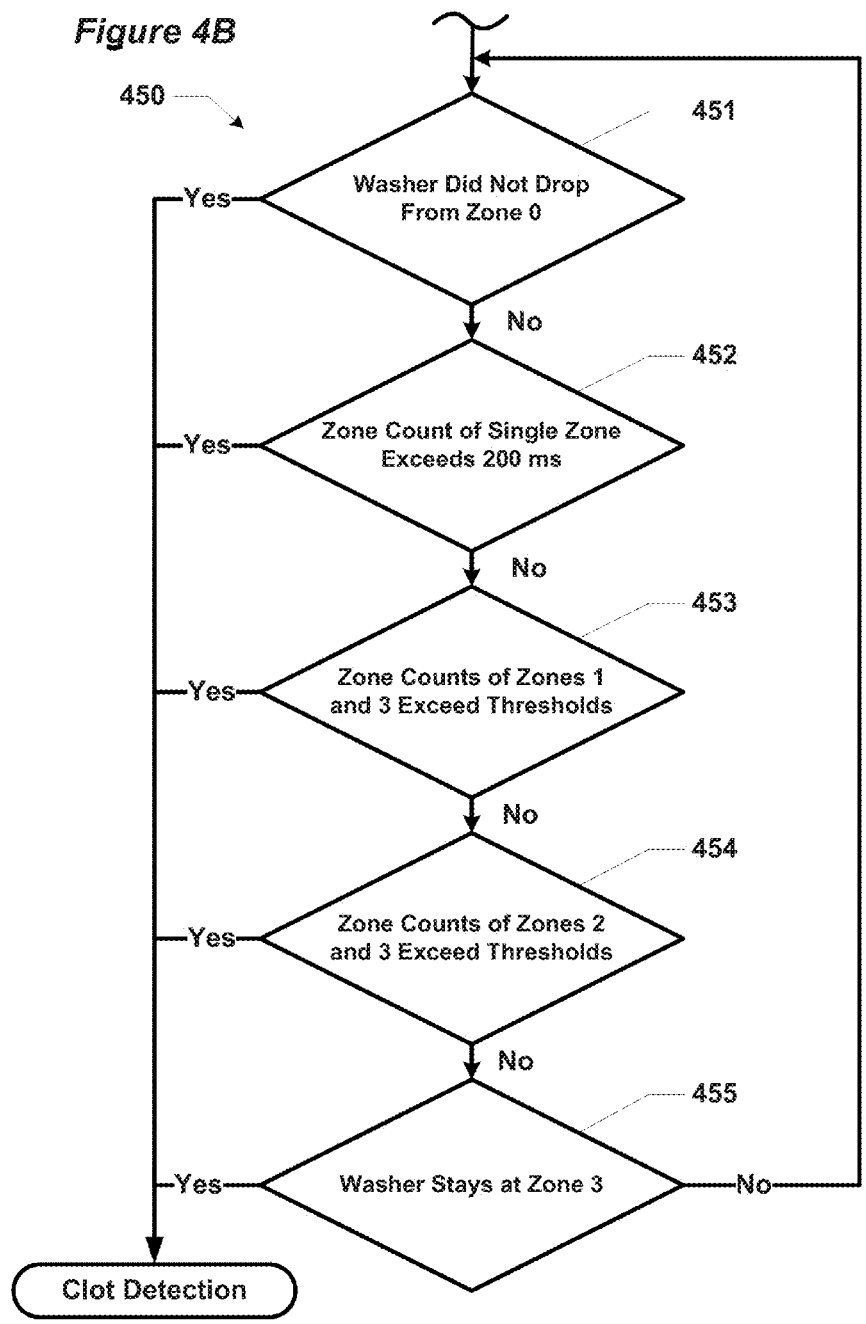

The geometry which underlies one possible initial clot detection algorithm is schematically illustrated in FIG. 3. The electromagnet 122, position detector 124, and fluid 200 have been omitted for clarity only. Similarly, the height of the chamber 114 is exaggerated relative to the thickness of the washer 116 only for purposes of illustration. The first embodiment of a clot detection algorithm which relies on this geometry is illustrated in the flowchart of FIGS. 4A-4B.

The clot detection algorithm 400 considers the total washer drop distance to be represented by a plurality of zones, such as four zones. The zones are not necessarily equally sized. In the embodiment illustrated, the four zones are (from top to bottom) labeled Zone 0, 1, 2 and 3. Because the total washer drop distance is determined by the geometry of the apparatus, it is determined at 410 in the following way: (1) the minimal and maximum locations of the washer are measured by the three initial lift and drop cycles before introduction of fluid 200; (2) the average values of the minimum (min) and maximum (max) are computed, and the initial washer travel distance is then calculated by the product of a factor and the difference between the maximum and minimum. The factor may be a hard-coded value slightly less than 1.0 (such as 0.91), so that the slight amount of time required for the washer to be released from the magnet is not included in the drop time; (3) the time of the washer dropping through the initial range [(0.91)×(max−min)] is measured and divided by 4 to yield a drop time for each of the four zones; (4) the end of zone positions are found by capturing the position values for each zone. The sample mix cycle is not required by the clot detection algorithm and therefore is not shown in FIG. 4A.

This embodiment thus relies on a calculation of disk velocity as the dependent variable, a value of distance as a constant, and time as the independent variable. As will be seen below, in an alternative embodiment, the roles of distance and time will be reversed.

The algorithm continues at 420 by determining the washer drop times (or, "zone counts") of an initial number of washer drops after the sample mix cycle described above. These values are summed together for each zone in the plurality of zones. A possible value for the initial number of washer drops is four.

Next, a sensitivity scale factor (1-100%) is invoked; this value is determined separately from the washer drop times and thus it may be hard-coded into the algorithm or preset in a parameter data file. The value of the sensitivity scale factor may vary over the course of the actual test cycles (discussed further below), but in this first embodiment the sensitivity scale factor is a constant.

Once the sensitivity scale factor is invoked, the clot detection threshold for each zone is calculated at 430 as the sum of the washer drop times of the initial number of drops, multiplied by the sensitivity scale factor.

The actual clot detection process then begins at 440. During the test phase, the washer is repeatedly lifted and dropped as in the conventional process described earlier. The washer drop times are counted on a per-zone basis for each of the plurality of zones that make up the total washer drop distance, as opposed to a single measurement based on the entire distance.

The clot detection algorithm may use the outcome of any one of a plurality of criteria applied at 450 to detect a clot. A possible number of criteria is five. Any criterion may or may not depend upon the sensitivity scale factor described above. Examples of criteria which do not depend upon the sensitivity scale include three criteria which identify non-movement of the washer: (a) at 451, the washer does not drop from the top, i.e., it remains in zone 0; (b) at 455, the washer does not rise from the bottom, i.e., it remains in zone 3; and (c) at 453, the washer moves too slowly through any zone, i.e., it is moving but does not leave any of zones 0-3 in less time than a threshold value. For example, in a system such that the washer in the absence of clots would have a drop time over the entire distance on the order of 200 msec or less, that value is a suitable threshold for any one zone; if the washer spends as much time in a single zone as it would be expected to spend over the distance represented by all zones in the absence of clotting, it is safe to assume that the washer is not moving due to the increased viscosity of the clotted sample.

Other criteria rely on the clot detection threshold that is derived from the sensitivity scale factor. Specifically, one criterion is that the zone counts of each of a pair of zones are greater than their respective clot detection thresholds. In another embodiment, more than one such pair of zones is established, i.e., two separate criteria of this type are considered. Such criteria may be: (d) at 453, the zone counts of zone 1 and zone 3 are each greater than their respective thresholds; and (e) at 454, the zone counts of zone 2 and zone 3 are each greater than their respective thresholds. Other combinations of zones may be selected in other embodiments. While either such criterion could be used as the (only) fourth criteria in addition to the three criteria above, they both may be used as the fourth and fifth independent criteria for detecting clot formation.

As noted before, taking all of the five criteria (a)-(e) together, any one such criterion may be used to consider a clot detected, but all five may be considered at once and any one of the five alone may be used to determine clot detection.

Figure 5:
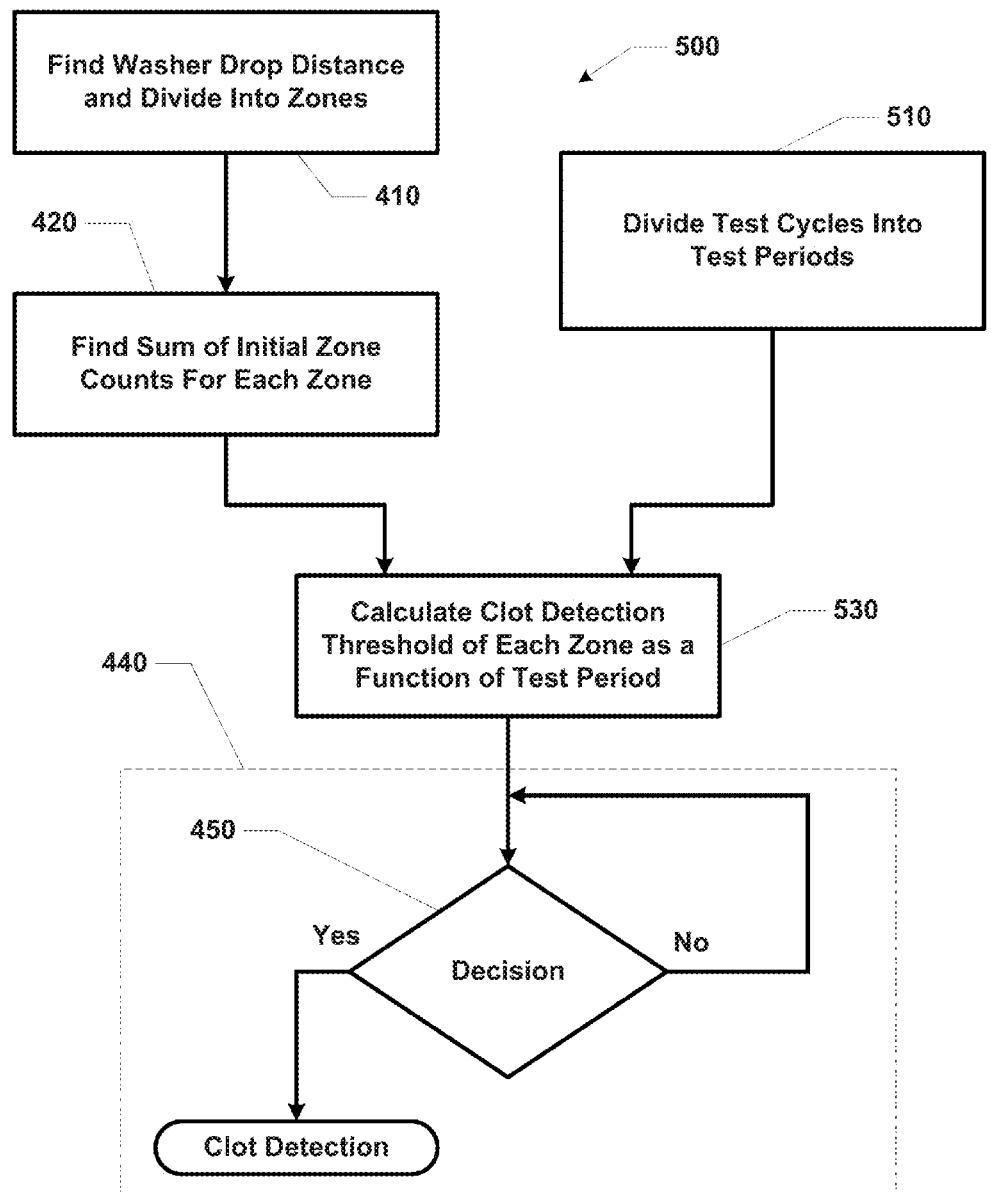
FIG. 5 is a flowchart of a second embodiment.

A second embodiment 500 is illustrated in the flowchart of FIG. 5. The second embodiment addresses a possible problem presented by using a constant sensitivity scale factor. If the constant value of the sensitivity scale factor is too low, false detection is possible, particularly during the initial test cycles when washer movements are not yet stabilized. This is because dry kaolin that is not fully mixed and dispersed during the initial mix cycle interferes with accurate assessment of the washer drop rates early in the test phase. However, if the value is too large, weak clots (i.e., clots which do not produce significant change in viscosity) may not be detected at all, particularly later in the test phase when the amount of unmixed dry kaolin is reduced by subsequent agitation during prior portions of the test phase.

To address this, the sensitivity scale factor (1-100%) may take on different values during different portions of the test phase in this second embodiment, as opposed to the first embodiment above, in which the sensitivity scale is a constant throughout the test phase.

Figure 6:
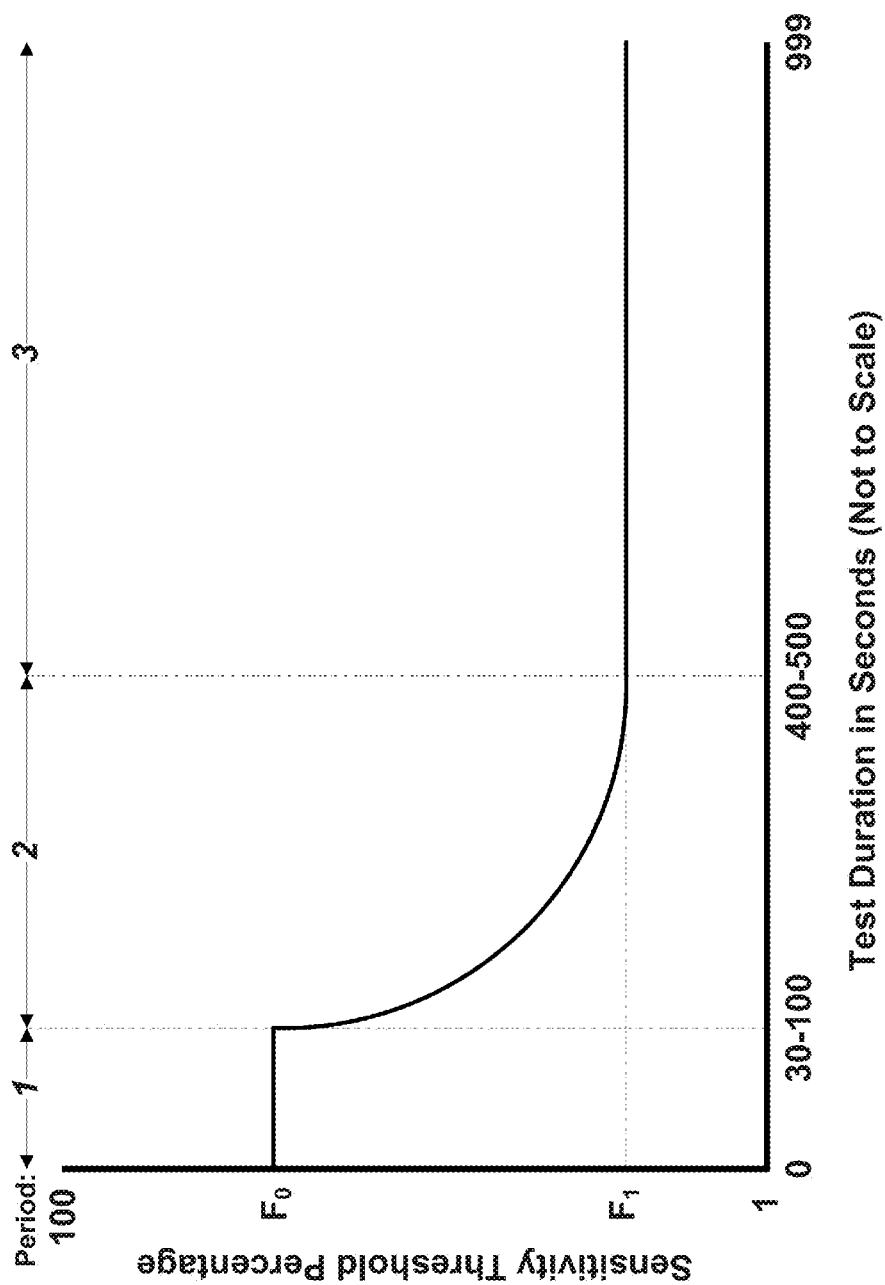
FIG. 6 is a schematic illustration of portions of the second embodiment.
Figure 7:
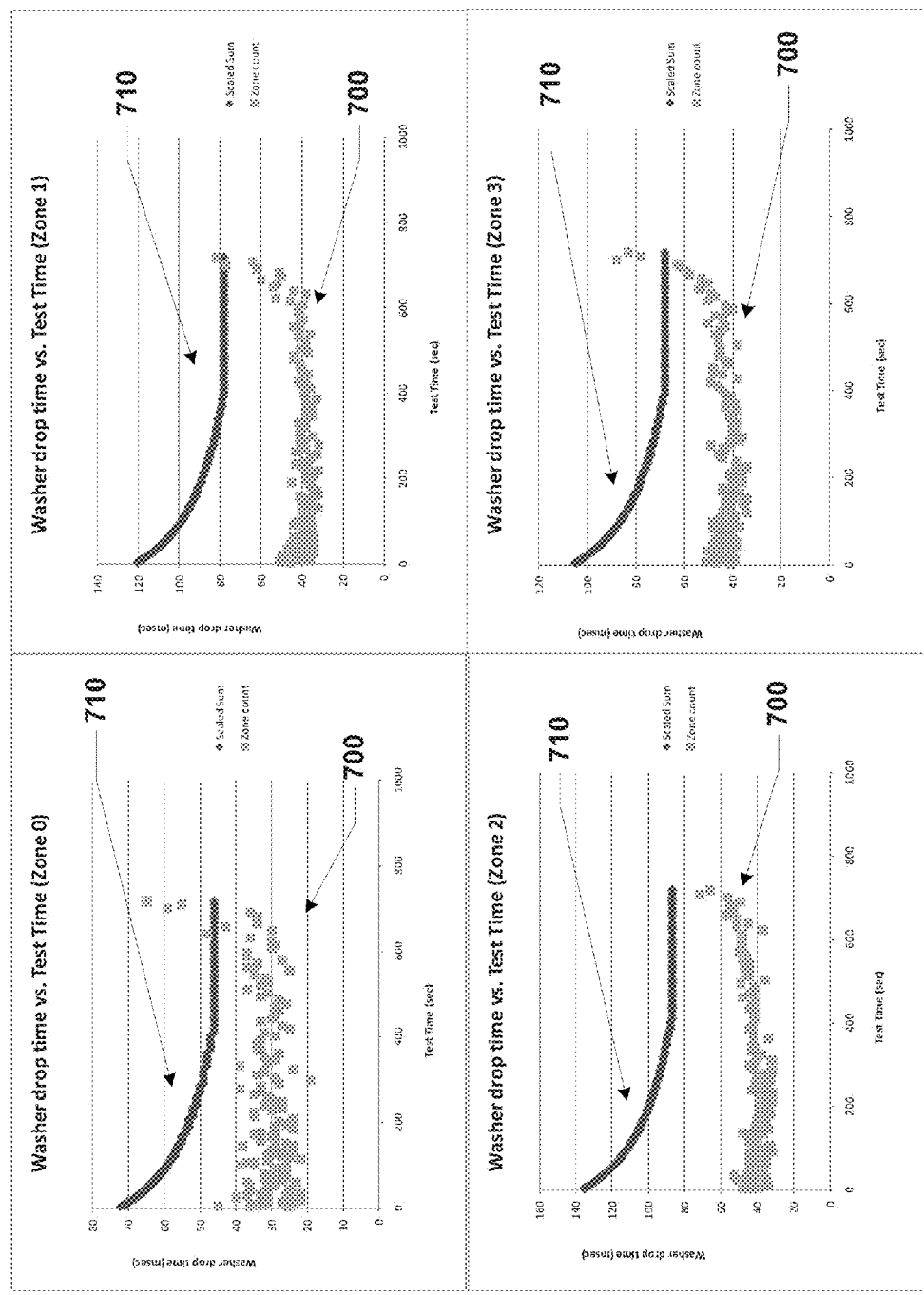
FIG. 7 is a set of four graphs, one for each of four zones, showing zone counts and scale factors as a function of time.

In an approach to this second embodiment, as illustrated schematically in FIG. 6, the coagulation test phase is divided into smaller periods; as illustrated, the entire test phase is divided into three test periods which are labeled 1, 2 and 3. The duration of each test period is either hard-coded into the algorithm or is a value obtained from a parameter file at 510.

At 530, the clot detection threshold is determined for each of the three periods. During the initial period, Test Period 1, which may be on the order of 0 seconds to a value in the range of 30 to 100 seconds, the clot detection sensitivity scale factor, $F_0$, may be obtained from a parameter file. A transition period, Test Period 2, begins at the end of Test Period 1 and may extend to a value on the order of 400 to 500 seconds in total elapsed time. During Test Period 2, the sensitivity scale is reduced from the initial value of $F_0$. The rate of reduction may be obtained from a parameter file. In general, the rate of reduction could be a constant value or a function of time or other parameters, such as an exponential decay. An exponential decay provides for a smoother transition. The final period, Test Period 3, begins at the end of Test Period 2 (if present, as illustrated) and extends to the conclusion of the test, typically 999 or 1,000 seconds. During Test Period 3, the sensitivity scale is constant at the reduced value $F_1$ which results from the steady reduction of the threshold value from $F_0$.

Thus, over the course of the three test periods, the sensitivity scale factor is relatively high during the first test period, which is typically when compounds (e.g., kaolin) are mixing with the blood and the washer location has not yet stabilized. The relatively high value avoids false detection of clots during such mixing. The lowered sensitivity in the third test period allows detection of weak clots. In the broadest implementation, only the initial and final (first and third) test periods are required; all that is required are relatively high and low values of the sensitivity scale factor. However, the second transition test period after the initial and before the subsequent final period will ensure a smooth transition between the two values. Although not illustrated here, additional periods (fourth, fifth, etc.) and scale factors values are possible but not required by this embodiment of the clot detection algorithm.

After the threshold value is determined for the current test period, the clot detection algorithm 450 is employed as described above.

Example 1

FIG. 6 shows an example of washer drop time monitored during a NG-HMS HR-ACT test as generally described above. This example shows how a clot is detected via the modified clot detection algorithm. In this example, a clot is detected by comparing washer drop times measured in Zones 1, 2 and 3 against the clot detection thresholds of their respective zones.

The pertinent data and parameters are summarized below. Initial threshold values were established at 30 seconds after the beginning of the test phase and final threshold values were established at 400 seconds (i.e., the transition period was 370 seconds in duration). The reduction in the threshold values was exponential at the rate indicated.

| Zone | Initial Four Values (msec) | | | | Sum of Four Zones (msec) | Initial Scale Factor | Initial Threshold (msec) | Final Scale Factor | Final Threshold (msec) | Percentage Reduction in Threshold from Initial | Final Zone Count at Time of Clot Detection |
|---|---|---|---|---|---|---|---|---|---|---|---|
| 0 | 24 | 24 | 24 | 24 | 96  | 75% | 72  | 0.4884 | 46 | 45% | 65 |
| 1 | 40 | 40 | 40 | 40 | 160 | 75% | 120 | 0.4884 | 78 | 43% | 82 |
| 2 | 45 | 45 | 45 | 45 | 180 | 75% | 135 | 0.4884 | 87 | 44% | 68 |
| 3 | 35 | 35 | 35 | 35 | 140 | 75% | 105 | 0.4884 | 68 | 43% | 83 |

The data in the table shows the drop times for the initial four drops in the each of the four zones. The drop times are scaled to the initial sensitivity scale factor to produce the initial threshold. As the scale factor is attenuated down, the threshold decreases for each zone (by 27% in this example). At the time of clot detection, the zone counts for Zone 1 and Zone 3 exceed their respective thresholds, and thus the criterion 453 (see FIG. 4B) has been met. Therefore, clot detection is triggered.

Figure 8:
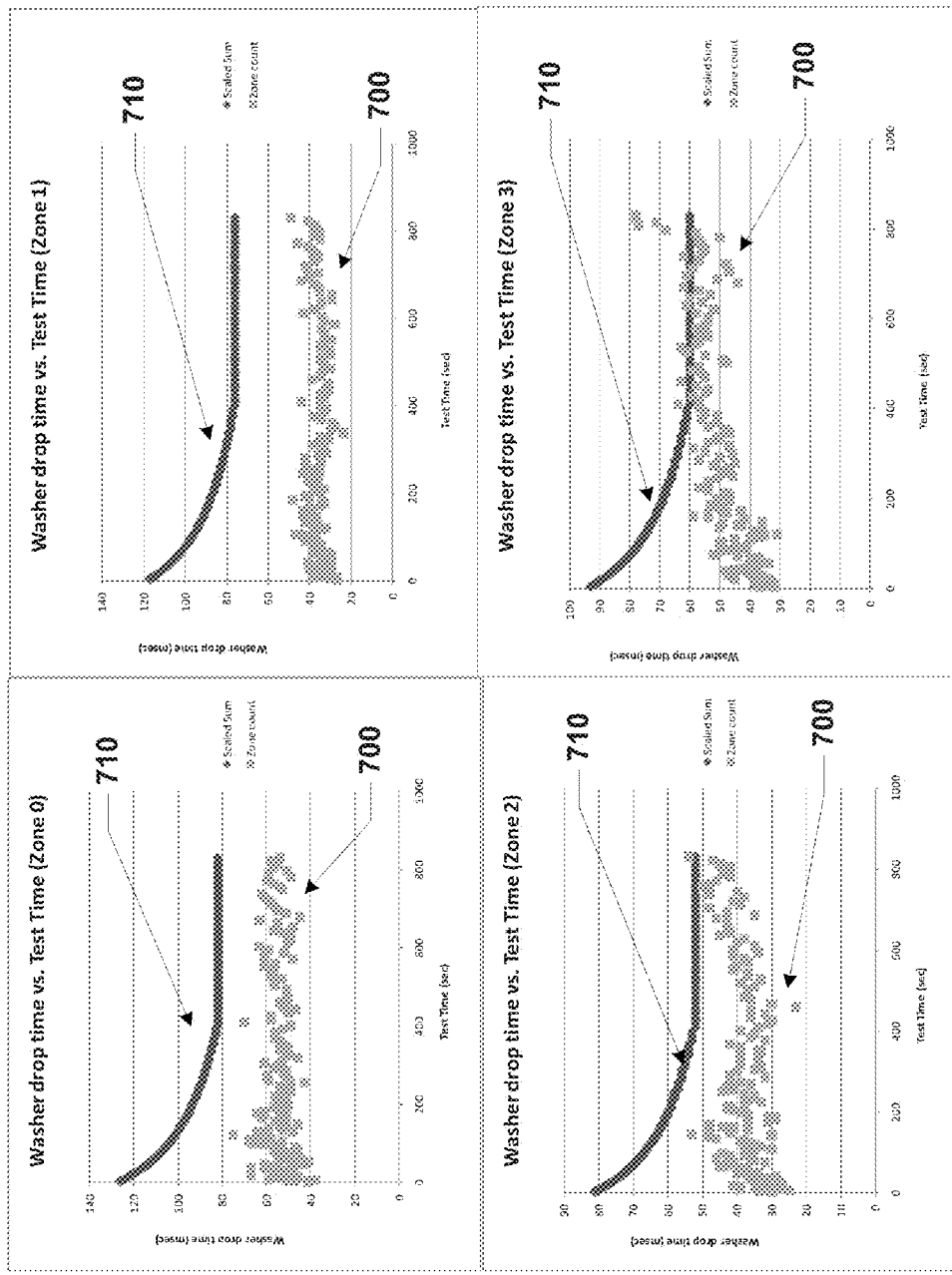
FIG. 8 is a set of four graphs, one for each of four zones, showing another set of zone counts and scale factors as a function of time.

The data in this example show that the washer drop times in each of the four zones generally decreased over the initial 400 seconds, then increased afterward. This is consistent with the dispersion of dry kaolin during the early portion of the test period. Kaolin reagent is not fully dispersed during the mixing period and therefore initially produces a longer drop time. When the kaolin is fully dispersed, the drop time decreases. After clot formation, the drop time increases (this is also illustrated in the data of FIG. 8). This illustrates why the individual zone threshold value needs to set high in the early portion of test period, so that the change in washer drop time caused by dry kaolin dispersion will not generate false clot detection. After the 400 second mark, as the threshold values are held constant at their respective reduced values, the increased washer drop times exceed the zone threshold values in zones 0, 1, and 3 after a cumulative time of approximately 750 seconds. The criteria for clot formation are met because the threshold values in both zones 1 and 3 are exceeded. In fact, for this specific data, in every case, the zone counts 700 exceeded the clot detection thresholds 710 during Test Period 3. This provides further support that alternative clot detection criteria could be formed from combinations of conditions other than those listed above.

A third embodiment is best explained with the following comprehensive description which repeats some of the description of the first two embodiments. However, this is solely for convenience and should not be understood to limit the scope of any embodiments of the invention in any manner. Thus, as before, the instrument or machine 10 is designed to measure the clotting capability of a patient's blood. The measurement is expressed as the amount of time it takes for a freshly drawn sample of blood to clot. The instrument operates using a disposable cartridge 100 that can hold a small amount of blood. The instrument keeps the cartridge 100 and blood sample 200 at a temperature equivalent to normal human body temperature. The cartridge 100 contains chemicals that accelerate the clotting of blood 200 in a known manner, so a clotting test can be completed quickly. The blood is injected at a syringe fitting on the cartridge, and fills a number of separate channels in the cartridge. In each channel, there is a well containing a metal disk or washer 116. The disk 116 is free to move up and down within the well 114. For each channel, the instrument has an electromagnet 122 positioned above the well that can be activated to lift the disk, or deactivated to drop the disk 116. There is also an inductive sensor 124 positioned below the well that can measure the vertical position of the disk in the well, and a capacitive sensor that detects when the well is full of blood.

To run a test of a blood sample's clotting capability, an operator will insert a fresh, unused cartridge 100 in the instrument and inject the blood 200. The instrument 10 then repeatedly accesses the electromagnets 122 to lift and drop each disk 116, while monitoring the disk position sensors 124 to evaluate the resulting movement of the disk. When the blood is first injected, each disk should be seen to freely move up and down in the well. As a test progresses and clots start to form in the blood, the movement of each disk should be seen to slow or stop due to interference from the clots. When the blood clots, the instrument outputs the elapsed test time that was required to achieve the clot. This is the desired measure of the blood sample's clotting capability.

There may be a number of different cartridge types used with the instrument. If so, typically each type has a specific mixture of chemicals designed for a specific type of clotting test. Some cartridge types use all channels, while others use only some of the channels. To support different cartridge types (if present), the instrument may be multi-functional, i.e., the operational methods (or "algorithm") performed by the computer processor connected to circuit board 300 may be parameterized. For example, numerous aspects of disk control and measurement are driven by configurable parameters. For each cartridge type, there is a unique set of predefined constants used to initialize the parameters when that cartridge is used. Key parameters that drive a test may present tradeoffs in setting the parameters for a specific type of cartridge. The system may have a separate copy of the cartridge configuration parameter settings for each defined cartridge type. The cartridge type may be indicated by a cartridge code number. The instrument may read or otherwise detect the number (e.g., by reading a bar code or similar indicia, or by other techniques) from the cartridge after it is inserted into the system.

As noted above, operation of the instrument involves both control of a disk (lift and drop), and measurement of the resulting disk behavior (span of distance traveled and velocity of drop). As before, fundamental terms for disk control and measurement may be defined.

Figure 9:
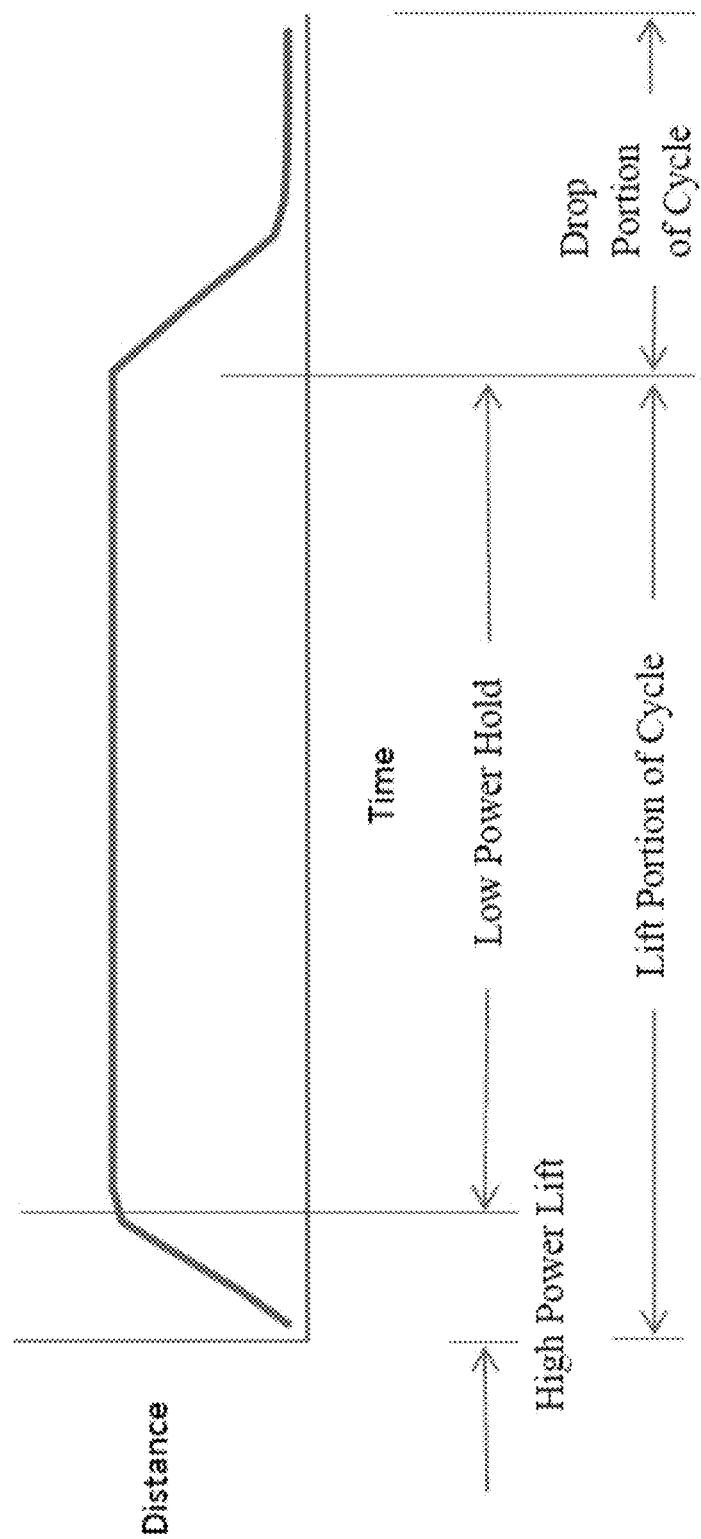
FIG. 9 is a schematic graph of the components of a Disk Cycle.

Referring to FIG. 9, a disk cycle is a time period over which a disk is lifted by the electromagnet, held at the top of the well for a while, and then dropped and allowed to settle. The lift portion of the cycle is the period of time from the beginning of the cycle until the disk is dropped. At the beginning of the lift, the electromagnet is activated with enough power to pull the disk up from within the well. Then the power is reduced to a minimal level to hold the disk at the top. The power is reduced to zero to drop the disk.

Figure 10:
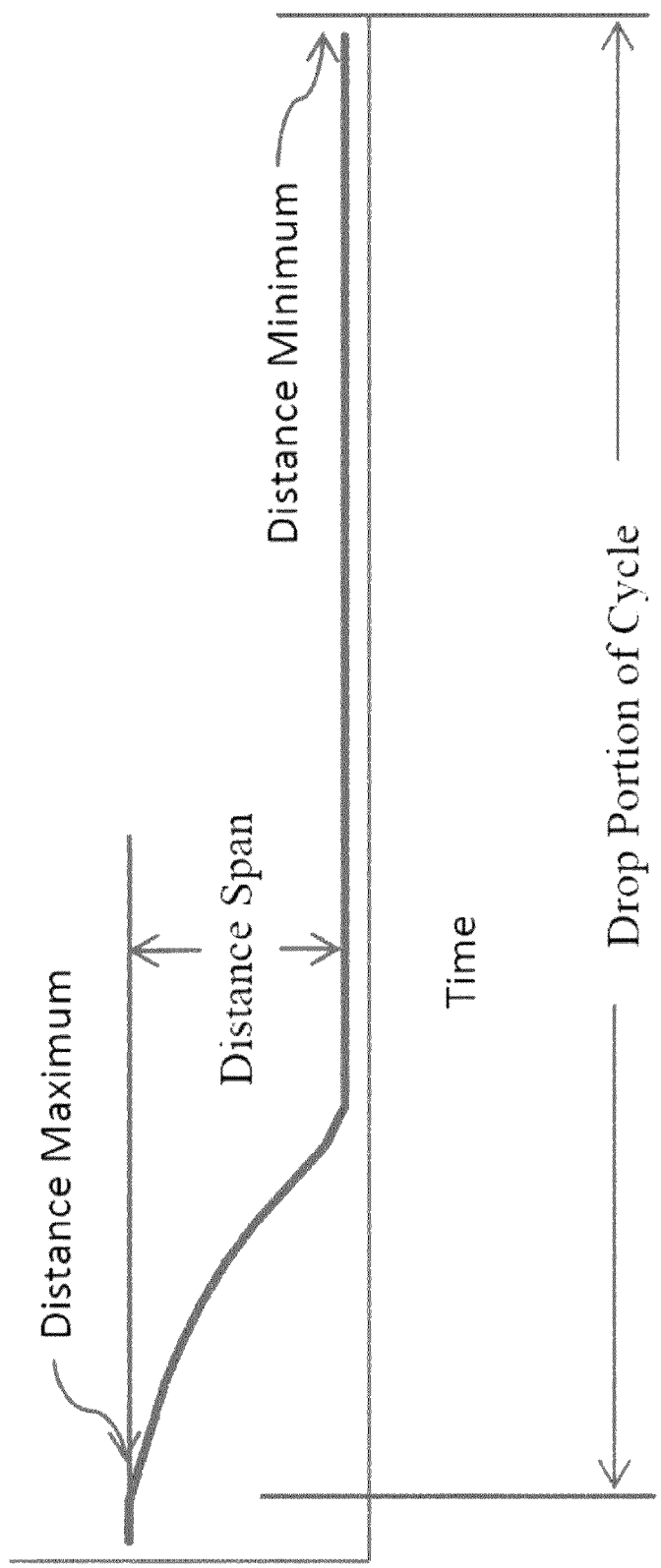
FIG. 10 is a schematic graph of the Disk Distance Span over the Drop Portion of a Disk Cycle.

Referring also to FIG. 10, during a disk cycle, the position sensor is accessed to determine values relating to the span of travel of the disk, such as Disk Distance Maximum (the vertical distance of the disk just before it is dropped), Disk Distance Minimum (the vertical distance of the disk after it is dropped and settles), and Disk Distance Span (the difference between Distance Maximum and Distance Minimum). Over the course of a test, a decrease in the Disk Distance Span is an indication that clots are forming and interfering with the span of travel of the disk.

Figure 11:
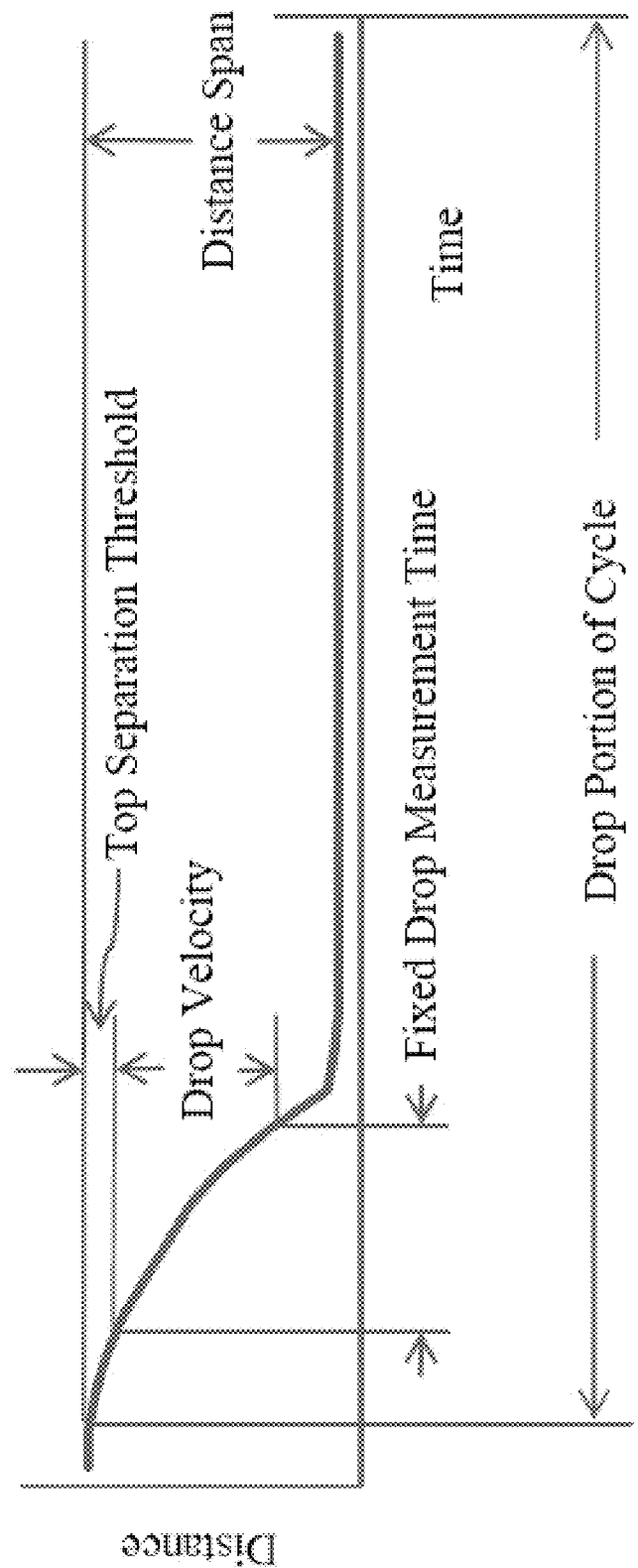
FIG. 11 is a schematic graph of parameters related to the Disk Drop Velocity.

Turning to FIG. 11, also during a disk cycle, the position sensor is accessed to determine values relating to the velocity of the disk during the drop, including Disk Drop Velocity (vertical distance dropped over a fixed Drop Measurement Time elapsed after the disk drops below a Top Separation Threshold). Since this value is computed as a distance traveled per unit of time, it can be called a velocity measure. The Top Separation Threshold and Fixed Drop Measurement Time are set to appropriate values during a Clot Test Calibrate operation as described further below.

As defined here, the Disk Drop Velocity is only a rough measure of the speed at which the disk dropped, but it is a reliable indicator of when the drop is being slowed by increasing viscosity of the blood sample due to clotting. An instantaneous measure of the disk speed is considered to be a less valuable indicator of clots, because it can vary widely among drops (even in the same sample at the same relative point in the disk cycle), due to variation in the way the disk drops (e.g., variation in the amount of time it takes to separate from the electromagnet, and/or variation in the angular orientation of the disk during the drop). These variations have a large effect on instantaneous speed measurements, but only minimal effect on the rough measure of speed. The velocity of the disk is of interest only during the drop portion of the cycle. During a drop, the force on the disk is its weight due to gravity, which is consistent from drop to drop. Thus, changes in the Disk Drop Velocity from drop to drop are directly due to changes in viscosity of the blood. During a lift, the force on the disk varies widely due to variations in its distance from the electromagnet, electromagnet power, angular orientation of the disk, etc. Thus, changes in disk velocity from lift to lift are not due to viscosity changes alone. For this reason, it is possible to forego measurements of the disk velocity during the lift. Use of the Disk Drop Velocity measure also provides more information about the state of the blood sample than the Disk Distance Span measure alone. The disk may continue to have the full span of travel from the top of the well to the bottom, but may slow significantly on the drops to the bottom. For some clot test types, the use of Disk Drop Velocity is critical to declaring the sample clotted at the correct elapsed test time.

Figure 12:
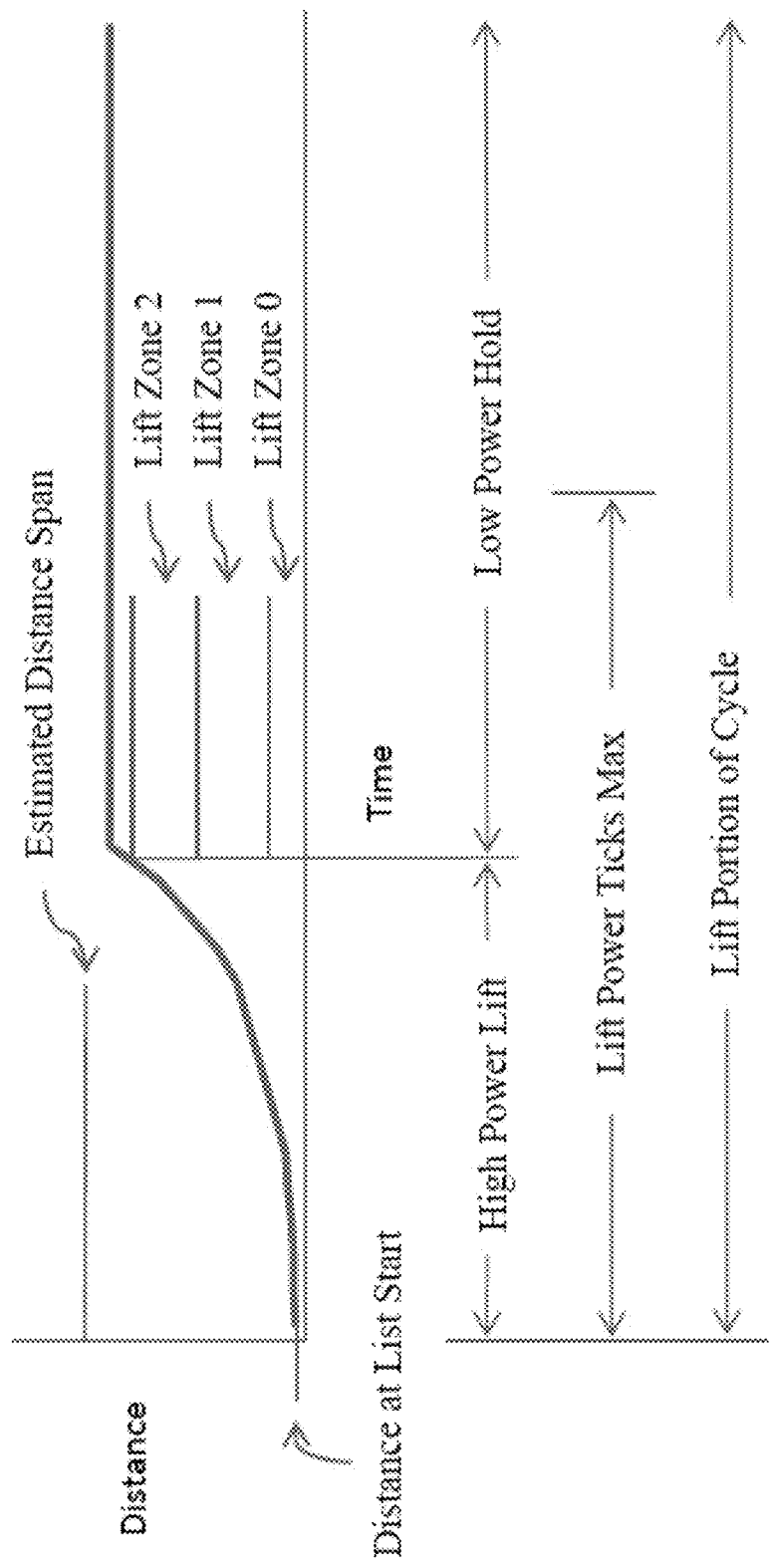
FIG. 12 is a schematic graph of parameters related to the Disk Scale.

Turning to FIG. 12, the Disk Scale is a set of scaling values relating to control of the disk during the lift. They determine how hard the electromagnet pulls on a disk during the lift portion of a cycle. The Disk Scale consists of the following values: Estimated Distance Span (the estimated distance span of the well), Distance At Lift Start (the distance value at the well bottom), Hold Power (the setpoint of the electromagnet power level after the high power lift is complete), and Lift Power Ticks Max (the maximum number of milliseconds in which electromagnet power can be set higher than the Hold Power at the beginning of the lift portion of a cycle). Several other remaining values allow for setting the electromagnet power higher than the Hold Power when the vertical distance of the disk is at a value lower than the top of the well. They include Lift Zone 0 Distance Span Max (span of distance from the well bottom comprising lift zone 0), Lift Zone 0 Power (setpoint of electromagnet power level when the disk is in lift zone 0), Lift Zone 1 Distance Span Max (span of distance from the well bottom comprising lift zone 1), Lift Zone 1 Power (setpoint of electromagnet power level when the disk is in lift zone 1, and not in zone 0), Lift Zone 2 Distance Span Max (span of distance from the well bottom comprising lift zone 2), and Lift Zone 2 Power (electromagnet power level to set when the disk is in lift zone 2, and not in zones 0 or 1). Other similar values can be established when there is a different number of zones.

The lift zone power levels are meant to be applied for only a brief period of time (for example, approximately 10 msec) to pull the disk to the top of the well. Once the disk is higher than the Lift Zone 2 Distance Span Max, the electromagnet power level is set to a Hold Power value. If the disk never gets higher than Lift Zone 2 Distance Span Max, the power is switched to Hold Power after the time period defined by Lift Power Ticks Max. Power levels higher than Hold Power are only allowed to be set for one cartridge channel at a time. The instrument sequences the channels one at a time to perform the disk lifts. The restrictions on electromagnet power ensure that the magnets do not generate heat in an amount sufficient to interfere with control of the blood sample temperature. The instrument may use a heater control loop to keep the blood sample at normal human body temperature.

Different settings of Disk Scale are used during the different phases of operation of a test (Cartridge Test, Mix, and Clot Test). The settings are changed to suit the purposes of the test phase. For example, during the mix phase, high power levels are used during the lift to agitate the blood for mixing with the dry chemicals in the cartridge. During the clot test phase, lower power levels are used so that lifting of the disks will not interfere with clot formation.

The instrument goes through three phases of operation to perform a test of a blood sample's clotting ability: Cartridge Test, Mix, and Clot Test.

When a cartridge is inserted into the instrument, the instrument performs a Cartridge Test to verify the disks all have a sufficient span of travel. The Cartridge Test consists of a series of steps. First, the Disk Scale is set to values appropriate for lifting the disks inside an empty cartridge (blood not yet added). The Estimated Distance Span value for each disk is set to a defined constant value, because there is no previous cycle data for this cartridge to give a better estimate. Next, a series (e.g., three) of Disk Cycles is performed. For each Disk Cycle, the following data are gathered and saved for each disk: Distance Minimum, Distance Maximum, and Distance Span. To pass the Cartridge Test, the data for each disk must conform to the following criteria: (1) each Distance Span must be greater than a defined minimum value; and (2) the maximum variation between any Distance Span and the largest Distance Span must be less than a defined maximum value. If the Cartridge Test passes, the average of the Distance Span values for each disk is saved, to be used as the Estimated Distance Span for the later test phases.

After the Cartridge Test, the instrument waits for the cartridge to be filled with blood by the operator. The fill sensors are polled until they indicate all channels are filled. When all channels are filled, the instrument begins the Mix phase of the test.

The purpose of the Mix phase is to agitate the blood in order to mix it with the dry chemicals contained in the cartridge wells. The Mix consists of the following steps. First, the Disk Scale is set to values appropriate for aggressively lifting the disks inside a blood-filled cartridge, and the Estimated Distance Span value for each disk is set to the average of the Distance Span values measured during the Cartridge Test. Next, Disk Cycles are performed for the time duration allocated for the Mix phase. The Elapsed Test Time begins counting at the beginning of the Mix phase. Later, when clotting is detected, the clotting time will be reported as the time since the beginning of the Mix.

In the Clot Test phase, the disks are lifted and dropped for the sole purpose of detecting when clots have formed in the blood. The Clot Test consists of the following steps. First, the Disk Scale is set to values appropriate for gently lifting the disks inside a blood-filled cartridge, and the Estimated Distance Span value for each disk is set to the average of the Distance Span values measured during the Cartridge Test. Next, Disk Cycles are performed for the time duration allocated to the Clot Test phase. For each cycle, various disk measurement data for each disk are temporarily saved. These include distance data for each 1 msec time increment of the first 500 msec of the drop portion of the cycle, if applicable. At the end of each cycle, the disk measurement data is used for one of two purposes, either a Clot Test Calibrate (in which the data is used for computing calibration values representing Distance Span and Drop Velocity of the blood sample in a normal unclotted state), or Clot Test Evaluate (in which the data is used for computing Distance Span and Drop Velocity for comparison against the calibration values, to determine if the blood sample has reached a clotted state). (Further details of Clot Test Calibrate and Clot Test Evaluate are discussed below.) The calibration data consists of three cycles worth of disk measurement values.

The decision about whether to use the disk measurement data for Clot Test Calibrate or Clot Test Evaluate is made as follows. If this is one of the first three cycles, then use the data for Clot Test Calibrate; but if this is not one of the first three cycles, but the current Distance Span is greater than the smallest Distance Span in the saved cycles of calibration data, then replace that cycle of Distance Span data with the current Distance Span for Clot Test Calibrate. This is necessary because the Distance Span can increase over the initial cycles of the Clot Test phase, as the dry chemicals continue to dissolve and allow for a greater span of travel of the disk. The calibration Distance Span must be recomputed to prepare for any clotting that occurs after this point. The calibration Drop Velocity is not changed from the value computed over the first three cycles. When replacing a Distance Span and redoing Clot Test Calibrate for the span, it is possible to follow that replacement with a Clot Test Evaluate. Since the new Distance Span is larger than the calibration value it replaced, it is unlikely that a clot will be detected due to a change in Distance Span, but a clot could be detected due to a change in Drop Velocity. If neither of the above two criteria are met, then the data is used for Clot Test Evaluate.

The purpose of the Clot Test Calibrate operation is to compute calibration values of Distance Span and Drop Velocity that represent normal values for the blood sample in an unclotted state. These values are best not computed until there are at least several (e.g., three) cycles of Clot Test drop data to analyze. In the case of three cycles, the calibration value for Distance Span is computed from the three available cycles of distance span data by taking the Distance Span calibration value as equal to the Largest Distance Maximum over the three cycles less the Smallest Distance Minimum over the three cycles. When a different number of cycles is used, an analogous calculation may be made. The calibration value for Distance Span is recomputed at every cycle where the new value of Distance Span is larger than one of the three values used for the previous computation of the calibration Distance Span. This is necessary because the Distance Span tends to increase during the early part of the Clot Test phase, as the chemicals in the cartridge well become fully dissolved. The calibration value for Drop Velocity is computed by analyzing the first three cycles of Clot Test drop data. The calibration value for Drop Velocity is computed only once for each disk. It is not changed when the calibration value for Distance Span is recalculated on a later cycle due to an increase in span.

Figure 13:
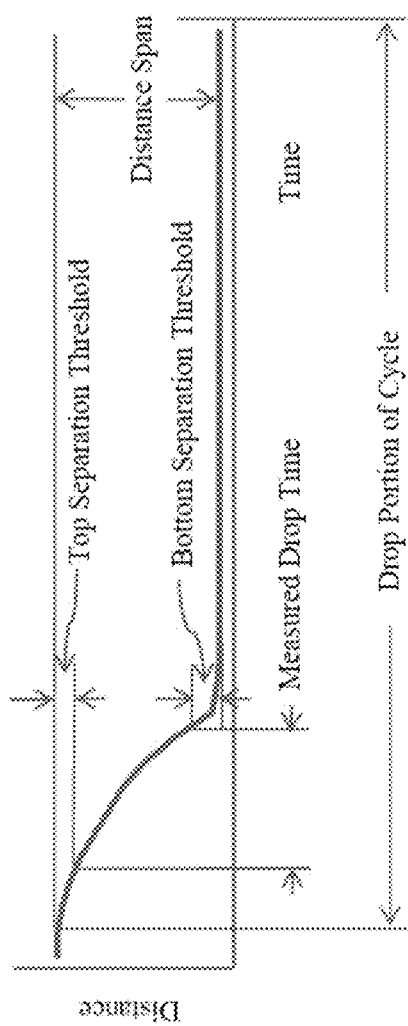
FIGS. 13 and 14 are schematic graphs of the Drop Velocity Calibration process in first and second passes, respectively.
Figure 14:
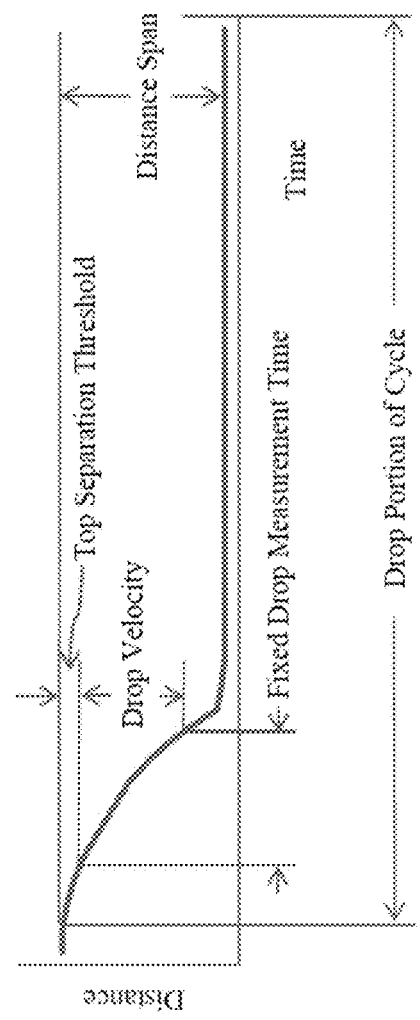

Referring now to FIGS. 13 and 14, the Drop Velocity is a rough measure of the speed at which the disk drops from top to bottom of the well. To compute the calibration value, the drop data is analyzed in multiple (e.g., two) passes. This allows the Drop Velocity measurement to be scaled to the characteristics of the specific cartridge well and fluid sample being used; the way that a disk drops can be quite different in one sample containing a whole blood fluid vs. another containing only blood plasma. In the first pass, the (three) cycles of drop data are examined to determine the Measured Drop Time for the disk to fall from top to bottom. To isolate this measurement from the normal signal noise of the position data, only a portion of the drop is considered. The Measured Drop Time is computed as a time that elapses after the disk falls below a Top Separation Threshold and before it enters a Bottom Separation Threshold. The Top Separation Threshold and Bottom Separation Threshold are computed from cartridge configuration parameters that define them as a percentage of the Distance Span. (Note that, while this implicitly creates three regions in the well, these should not be confused with the Zones established in the alternative embodiment discussed above.) The average of the Measured Drop Time values over the (three) cycles is used as the Fixed Drop Measurement Time for the second pass.

In the second pass, a Drop Velocity value is computed for each of the (three) cycles of drop data. Each Drop Velocity is computed as the vertical distance dropped over a Fixed Drop Measurement Time elapsed after the disk drops below a Top Separation Threshold. The calibration value of Drop Velocity is then set to a representative value, such as the largest of the Drop Velocity values computed over the (three) cycles of drop data. (In other variations, the representative value could be the average or mean of the values.) The Fixed Drop Measurement Time and Top Separation Threshold are saved for computing Drop Velocity values in Clot Test Evaluate operations throughout the remainder of the Clot Test.

It bears repeating that this embodiment, in contrast to the "Zoned" embodiment discussed above, relies on a calculation of disk velocity as the dependent variable, taking distance as the independent variable and time (specifically the Fixed Drop Measurement Time value) as a constant.

In order to pass the Clot Test Calibrate, the data for each disk must conform to the following: each Distance Span must be greater than a defined minimum value, the maximum variation between any Distance Span and the largest Distance Span must be less than a defined maximum value, each Drop Velocity must be greater than a defined minimum value, and the maximum variation between any Drop Velocity and the largest Drop Velocity must be less than a defined maximum value. If the Clot Test Calibrate fails, then the channel will be indicated as already being clotted. Otherwise the channel will continue to be processed in the Clot Test phase.

The purpose of the Clot Test Evaluate operation is to compare the current values of one or both of Distance Span and Drop Velocity to their respective calibration values, to determine if the channel is clotted. The exact criteria used when comparing the current values to the calibration values are specific to each cartridge type, and are therefore defined in the Cartridge Configuration Parameters when that approach is employed. Specifically, the Cartridge Configuration Parameters define which one of the following sets of changes must occur in order for a channel to be declared clotted: (1) if Distance Span drops below a threshold value, defined as a percentage of the calibration Distance Span; (2) if Drop Velocity drops below a threshold value, defined as a percentage of the calibration Drop Velocity; (3) if either Distance Span or Drop Velocity drops below its respective threshold value, i.e., either (1) or (2); and (4) if both Distance Span and Drop Velocity drop below their threshold values, i.e., both (1) and (2). Once a channel is declared clotted, its elapsed clotting time is captured and the channel no longer undergoes Disk Cycles in the Clot Test phase.

For either Distance Span or Drop Velocity, one variation is to require that the clot detection threshold be reached for a number of consecutive cycles before a clot is declared. In that case, a further option is to use a specific one of those cycles as the cycle representing the elapsed clotting time. With this feature, a single low measurement of Distance Span or Drop Velocity might not result in a reported clot, but if that measurement persists for a number of consecutive iterations, then the first occurrence of the measurement could be indicated as the clotting time. This is a way to guard against an anomalous event that might affect the measurement of a single cycle.

Other aspects of the first and second embodiments discussed above are also applicable to this third embodiment. For example, over the course of the test it is possible to do any or all of: change (especially, to increase) the cycle times, change lift power levels, and change clot detection thresholds, for the same reasons as noted above and using the same or equivalent techniques. For example, the clot detection sensitivity scale factor, or any other parameter relevant to at least one of the plurality of criteria used to determine clot formation, may be changed in a manner analogous to that illustrated in FIG. 6. This includes optional variations such as holding the parameter equal to a first constant value during an initial period of the plurality of periods, and at a second constant value (lower than the first constant value), during a subsequent third period of the plurality of periods; the initial period and the subsequent period may be separated by a transition period during which the parameter is reduced from the first constant value to the second constant value. The parameter may be reduced during the transition period at a constant rate, or exponentially, during the transition period.

Figure 15:
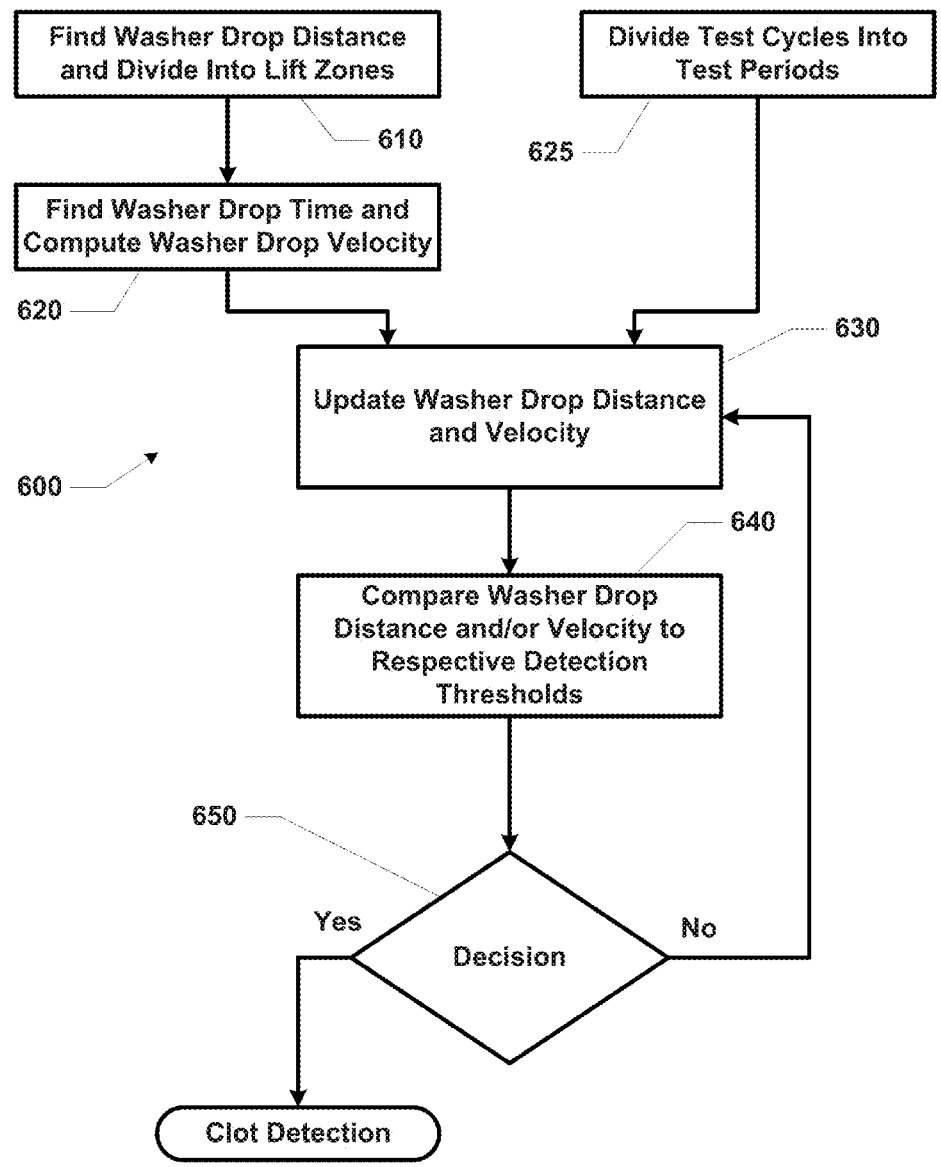
FIG. 15 is a flowchart of a third embodiment.

FIG. 15 is a summary 600 of this third embodiment as described in detail above, in a flowchart form analogous to that of FIG. 5 for the second embodiment. At 610, the washer drop distance is found and divided into lift zones. At 620, the washer drop time is found and thus the washer drop velocity is computed. Separately, at 625, the test cycles are divided into test periods. These two inputs enter step 630, in which the washer drop distance and velocity values are updated if appropriate, and then into 640 in which the washer drop distance and/or velocity are compared to their respective threshold values. Based on such comparison(s), the decision 650 is made whether to consider the clot detected or to continue the testing (updating values as noted before).

Figure 16:
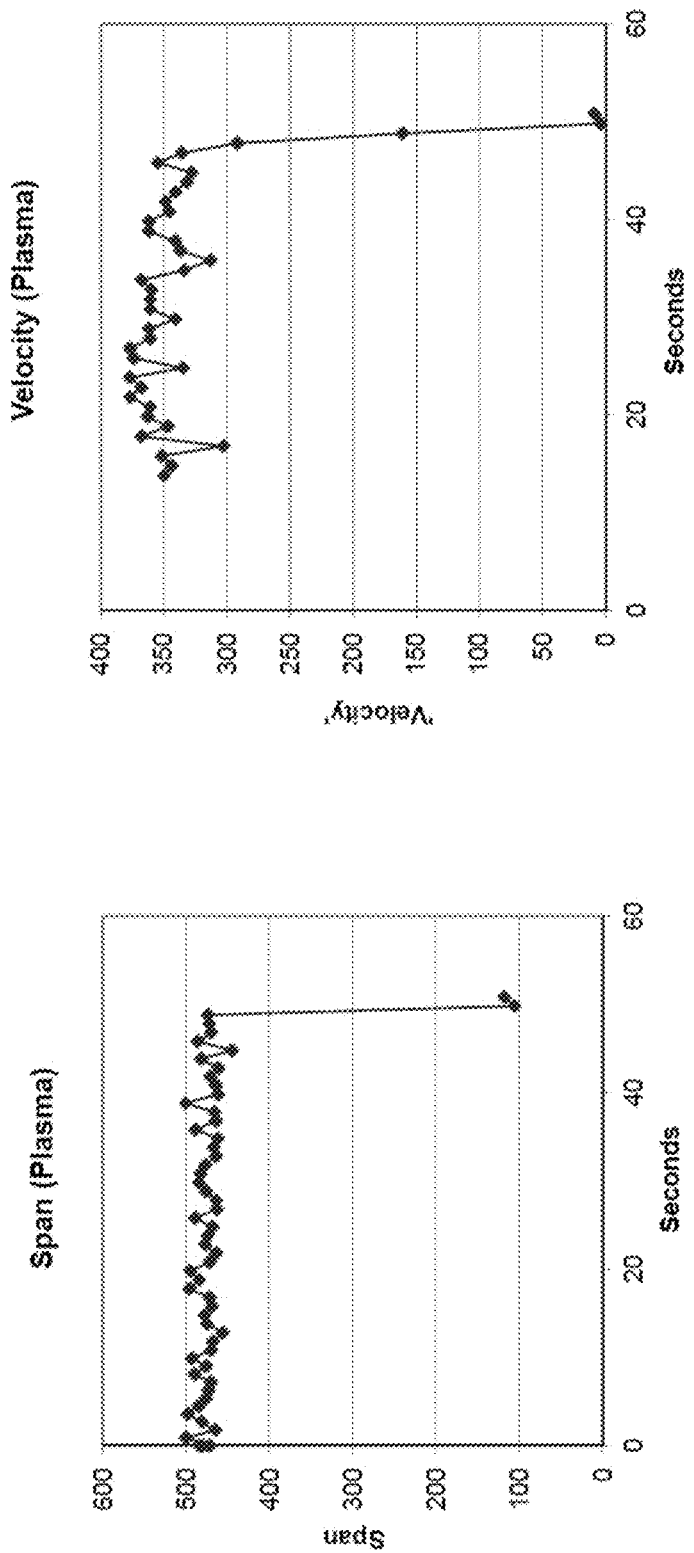
FIGS. 16-18 are sets of paired graphs (two graphs in each figure), showing measurements of various results of testing of the third embodiment.
Figure 17:
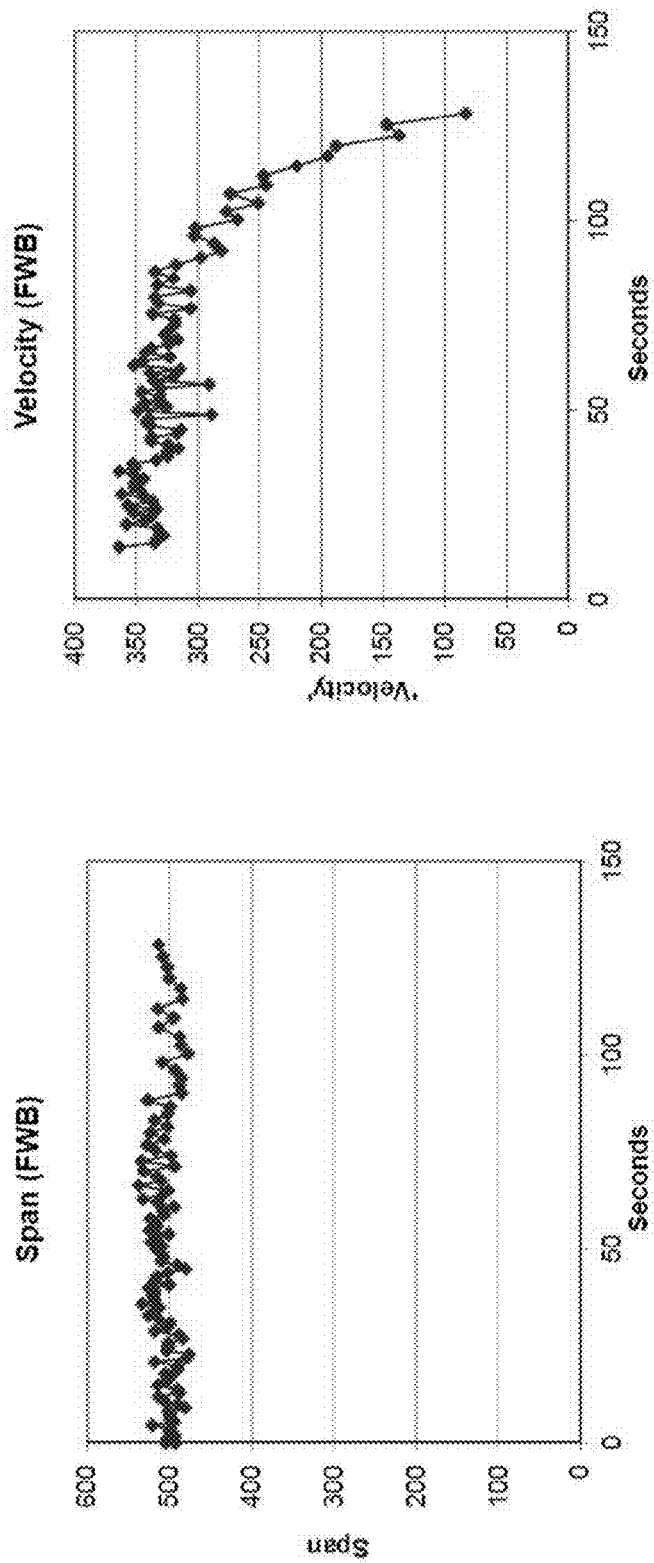

FIGS. 16-17 illustrate the importance of considering either or both of washer travel distance (span) and velocity, depending on the assay and identify of sample fluid being tested. Each figure is a pair of graphs comparing results of test measurements related to the third embodiment. FIG. 16 illustrates measurements of washer travel distance (span) on the left and washer velocity on the right, both measured in plasma from a common sample and in the same channel of a test apparatus. As can be seen, the steep and sudden decrease span and velocity after approximately forty-five seconds demonstrates that either parameter could be used to detect a clot, and further that the combination of the two parameters could be also be used. By contrast, FIG. 17 is a similar illustration of those two parameters in samples of fresh whole blood ("FWB"), again in a common channel. A comparison of the two graphs shows that even if span length remains essentially unchanged (left graph), a sudden decrease in washer velocity (right graph) may be used alone to signal clot formation.

Figure 18:
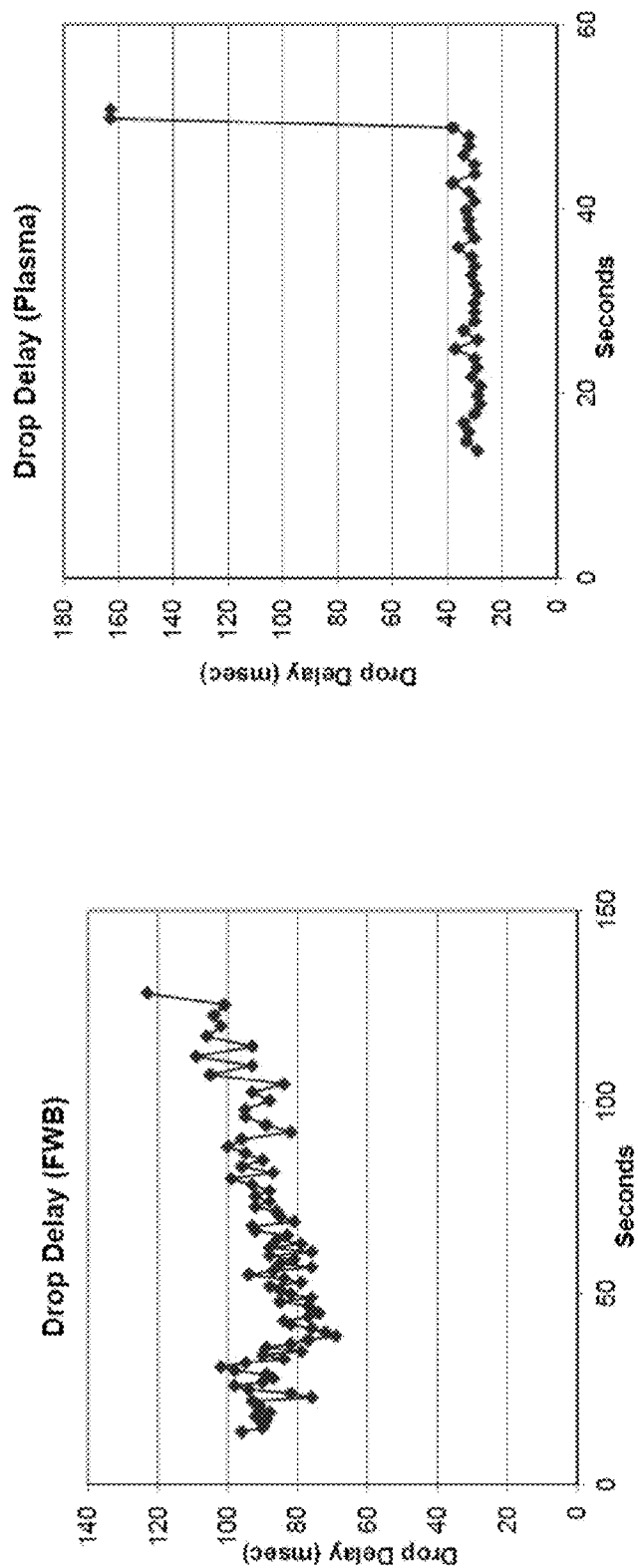

FIG. 18 compares the drop delay time (i.e., the time in the top separation zone) between samples of FWB (on the left) and plasma (on the right) in different channels. It illustrates that the former is relatively insensitive to change with time, even times as long as nearly 150 seconds; whereas the latter exhibits a sudden and dramatic increase from a very stable value (approximately 30 msec on average) after approximately 50 seconds of test duration. The results show that the washer drop delay time is dependent on viscosity because the values are significantly greater for FWB than for plasma. The average fixed drop measurement time in the unclotted plasma in this example was 40 msec and for the unclotted FWB it was 107 msec.

While the description above uses the procedures and values of clot detection algorithms to describe certain details, the broadest scope of the disclosure includes physical representations of that algorithm (such as an apparatus which relies on any combination of analog or digital hardware to implement the same), as well as methods of carrying out the algorithm that do not depend upon the specific physical components mentioned above but nonetheless achieve the same or equivalent results. Therefore, the full scope of the invention is described by the following claims.

What is claimed is:

1. A method of detecting formation of a clot in a blood sample with a washer dropping over a distance through the sample, comprising:
   a. dividing the distance into a plurality of zones;
   b. during a plurality of initial cycles, dropping the washer repeatedly through the distance and determining an initial drop time for each of the zones;
   c. calculating a clot-detecting threshold for each zone by multiplying its initial drop time by a scale factor, wherein the scale factor may be the same or different for one or more time periods of the test;
   d. for each zone and each time period, measuring a plurality of zone drop times of the washer dropping through the zone;
   e. declaring clot formation when at least one measured zone drop time is greater than the corresponding threshold.

2. The method of claim 1, wherein the one or more time periods of the test comprise at least a first period and a second period, and wherein the scale factor of the first period is equal to a first constant and the scale factor of the second period is equal to a second constant less than the first constant.

3. The method of claim 2, wherein the first period and the second period are separated by a transition period, and wherein the scale factor of the transition period is less than the first constant and greater than the second constant.

4. The method of claim 3, wherein the scale factor of the transition period is reduced with time at a constant rate.

5. The method of claim 1, wherein step e comprises declaring clot formation when the measured zone drop time of each of at least two zones is greater than the corresponding threshold.

6. The method of claim 1, wherein the initial drop time for each of the zones is an average over the initial cycles through that zone.

\* \* \* \* \*